United States Patent [19]

Taheri

[11] Patent Number: 5,042,707

[45] Date of Patent: Aug. 27, 1991

[54] INTRAVASCULAR STAPLER, AND METHOD OF OPERATING SAME

[76] Inventor: Syde A. Taheri, 268 Dan Troy, Williamsville, N.Y. 14221

[21] Appl. No.: 598,245

[22] Filed: Oct. 16, 1990

[51] Int. Cl.$^5$ ............................................. A61B 17/00
[52] U.S. Cl. ............................. 606/213; 227/175; 227/178; 227/179; 227/19
[58] Field of Search ................ 227/19, 175, 179, 178; 606/219

[56] References Cited

U.S. PATENT DOCUMENTS

| | | | |
|---|---|---|---|
| 4,473,077 | 9/1984 | Nolies et al. | 227/179 |
| 4,477,007 | 10/1984 | Foslien | 227/19 |
| 4,485,817 | 12/1984 | Swiggett | 227/179 |
| 4,488,523 | 12/1984 | Shichman | 22/179 |

Primary Examiner—Stephen C. Pellegrino
Assistant Examiner—Gary Jackson
Attorney, Agent, or Firm—Sommer, Oliverio & Sommer

[57] ABSTRACT

An articulatable stapler (20) is arranged in the form of an elongated catheter having a plurality of segments (25,26,28) mounted on one end of a catheter main body (24). A stylet (64) is slidably received within the catheter main body and two intermediate segments, and may be selectively moved to articulate the segments such that the most-distal segment is either aligned with, or arranged at a substantial angle with respect to, the catheter main body portion. The most-distal segment (28) carries stapling means (30) by which the improved catheter may cause a staple to be inserted through a graft (89) into the wall of the blood vessel. The improved device also has means for selectively bending a staple (75) so as to prevent unintended separation therefrom.

12 Claims, 3 Drawing Sheets

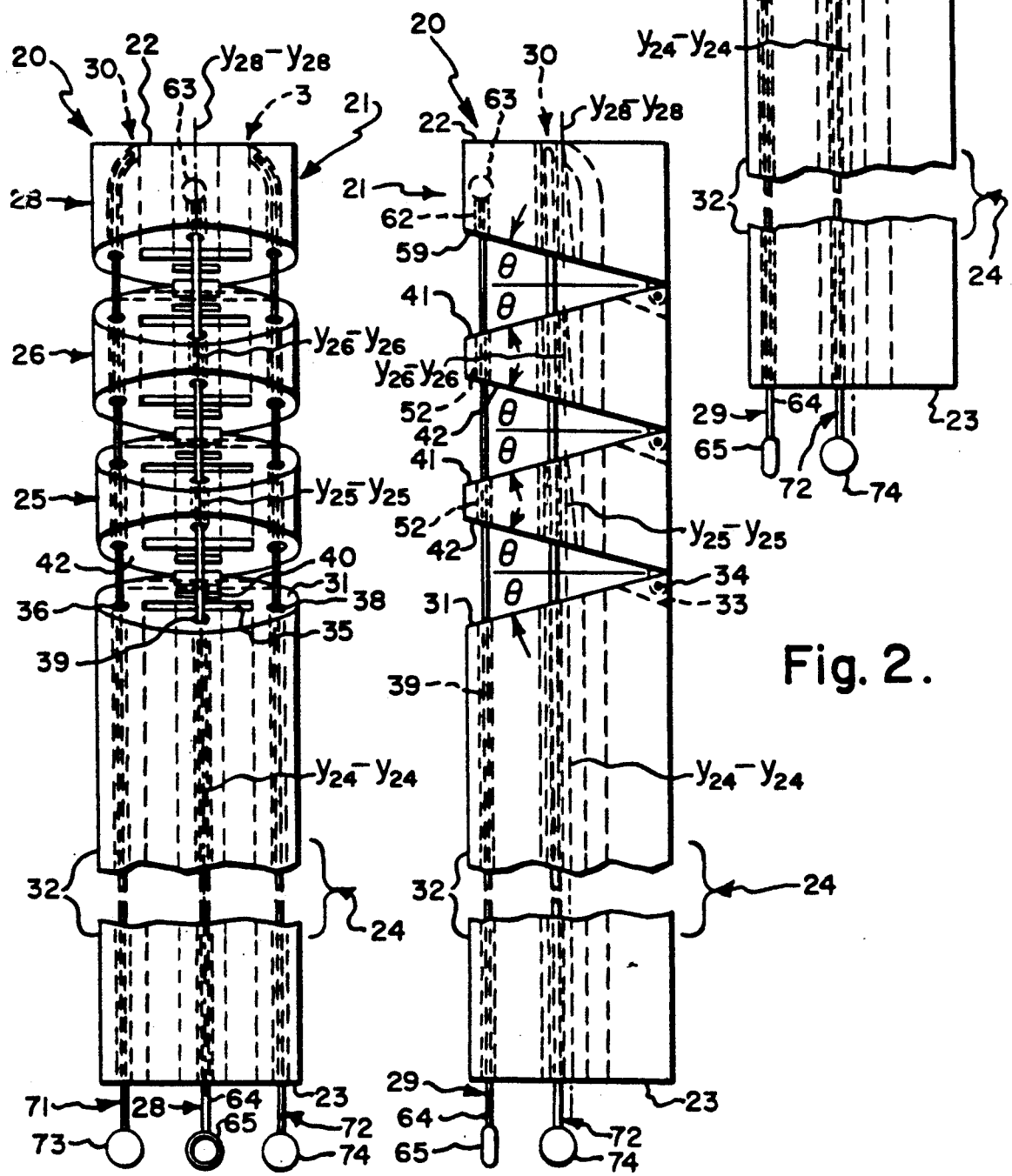

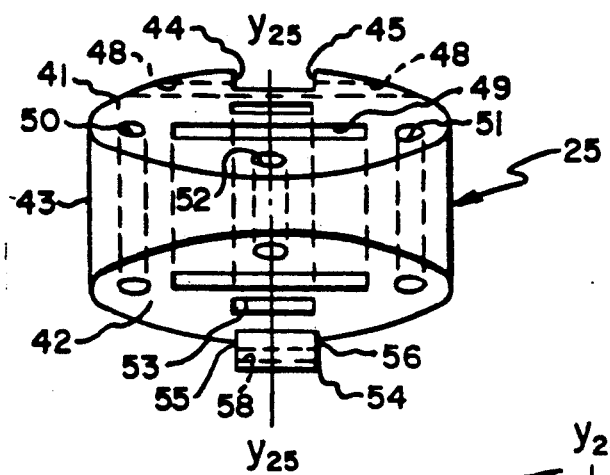
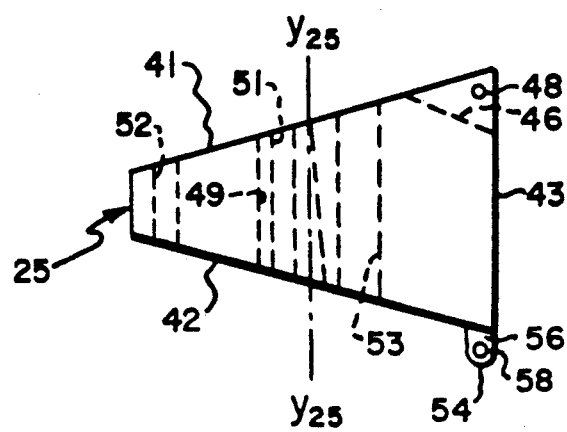
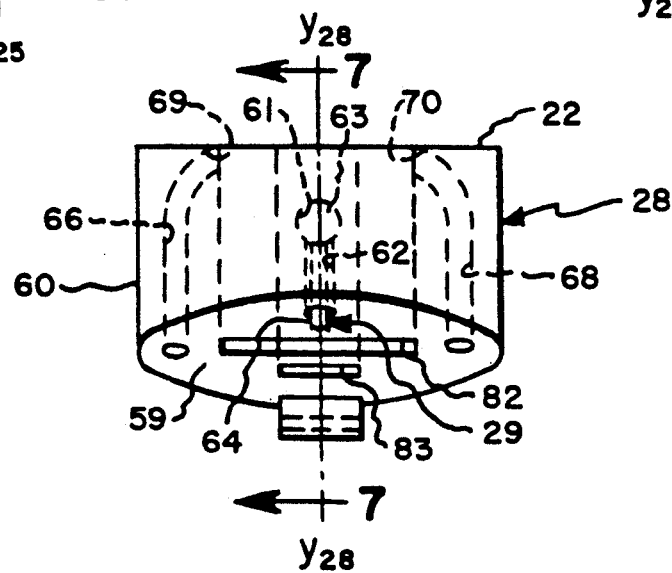
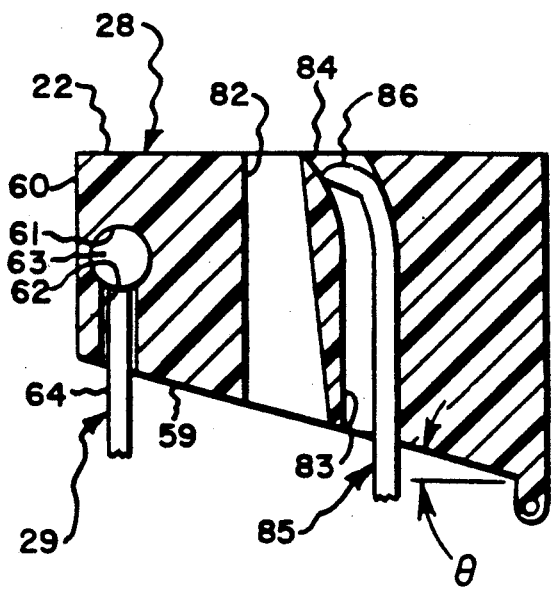
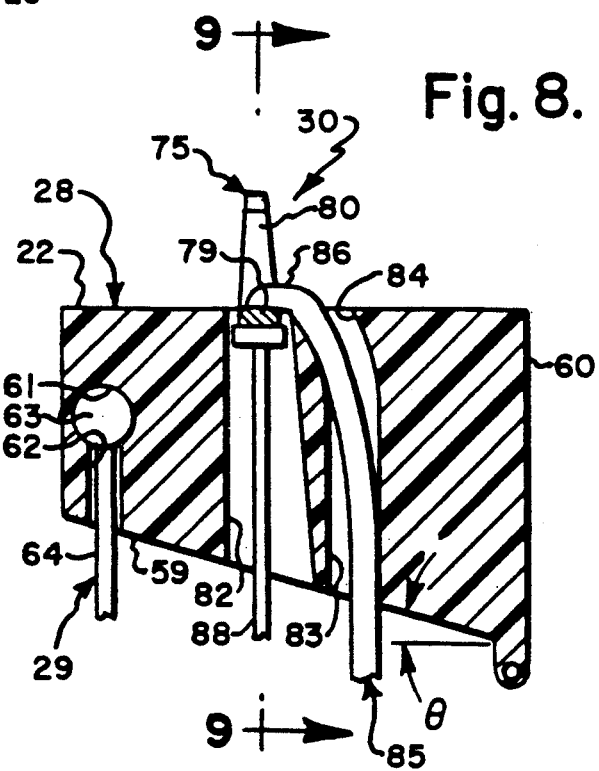

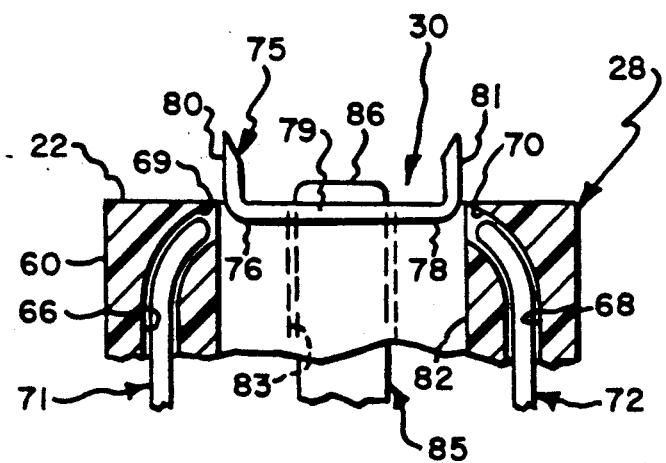
Fig. 9.
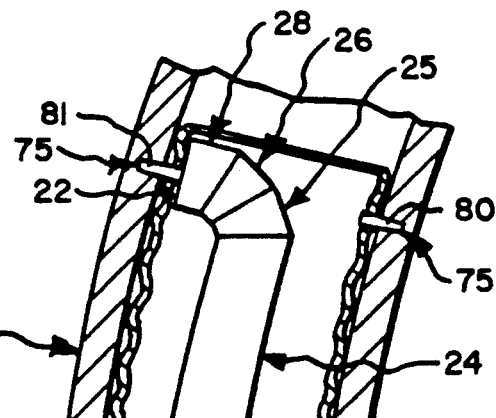
Fig. 12.
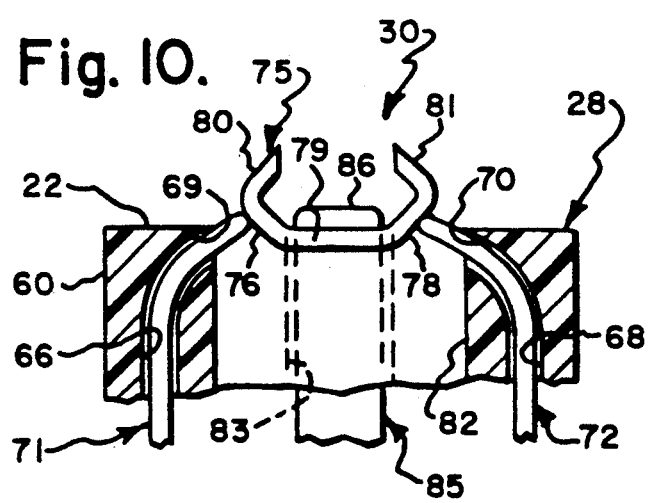
Fig. 10.
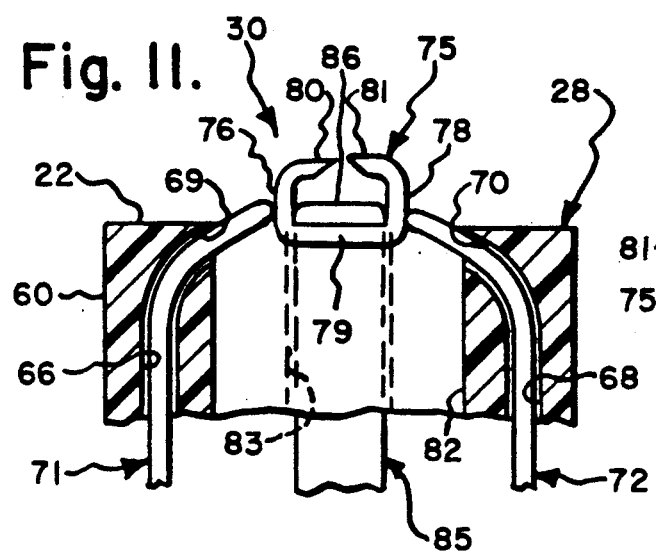
Fig. 11.
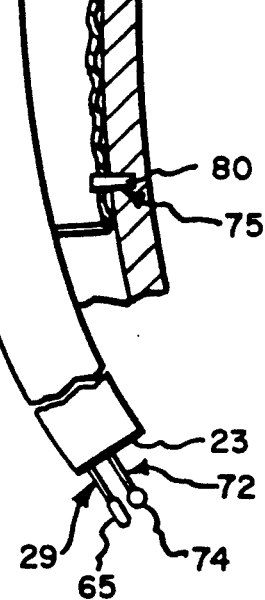

INTRAVASCULAR STAPLER, AND METHOD OF OPERATING SAME

TECHNICAL FIELD

This invention relates generally to the field of surgical staplers, and, more particularly, to an improved stapler which is adapted to be inserted into a blood vessel and moved to a desired position therealong, and having a selectively-articulatable distal marginal end portion which may be used to staple an object (e.g., tissue, a graft, etc.) to the interior wall of the blood vessel.

BACKGROUND ART

Surgical staplers have been developed in recent years, and are now recognized as providing a viable alternative to suturing. Upon information and belief, the principal advantage of stapling vis-a-vis suturing lies in a saving of time on behalf of the surgeon.

Some suture materials are soluble in body fluids, while other suture materials are not. In the case of the so-called dissolving suture, the various stitches may be permanently enclosed within the body. After passage of time, normally long enough for the joined tissue to heal, the suture will gradually dissolve. Stitches of non-dissolving suture, on the other hand, must generally be physically removed.

Staples are normally formed of metal. Some metals, such as stainless steel, platinum or titanium, are generally recognized as being non-thrombogenic, and may simply be left within the patient's body. After the stapled tissue heals, the staples are no longer needed for their intended initial function, and may simply remain within the body. If they are made of a non-thrombogenic material, their retained presence within the body is not adverse.

In the past, various types of special-purpose staple guns have been developed. These various types are arrayed in "Stapling Techniques-General Surgery", Third Edition (United States Surgical Corporation 1988). Additional illustrations of prior art stapling techniques may be found in Soper et al., "A Stapled Technique for Construction of Ileal J Pouches", *Surgery, Gynecology & Obstetrics* (June 1988) [pp. 557-559], Kataoka et al., "Problems Associates with the EEA Stapling Technique for Esophagojejunostomy After Total Gastrectomy", *Ann Surg.* (January 1989) [pp. 99-103], and Brough et al., "An Improved Technique of J Pouch Construction and Ileoanal Anastomosis", *Br. J. Surg.* (April 1989) [pp. 350-351].

At the same time, techniques have been developed for repairing a damaged blood vessel by placement of a tubular graft therewithin. The graft itself is typically formed of suitable fabric, and is in the shape of an elongated thin-walled cylindrical tube. According to one technique, the graft may be furled upon a stylet, inserted longitudinally in a patient's blood vessel through a suitable incision in same, and, once in the desired position relative to the blood vessel, may be suitably unfurled to reassume its cylindrical shape within the blood vessel. It is thereafter necessary to secure the graft to the wall of the blood vessel. In this regard, my prior U.S. Pat. No. 4,872,874 ("Method and Apparatus for Transarterial Aortic Graft Insertion and Implantation") discloses a technique for stapling the opposite marginal end portions of such a tubular graft to the vessel wall. Basically, my earlier patent discloses, in pertinent part, a plurality of radially outwardly-facing U-shaped staples operatively held in an inflatable bulb. After the graft has been initially positioned, the deflated bulb is inserted into the blood vessel. Once in the desired position, the bulb is thereafter inflated to drive the staples radially outwardly, thereby to join the marginal end portions of the graft to the vessel wall. In that prior arrangement, when the bulb is inflated, the staples are driven radially outwardly into engagement with the vessel wall, but the legs of the staples are not bent, crimped or otherwise deformed after penetrating the graft and blood vessel. Basically, the U-shape of the staples was unchanged after the tips of the legs penetrated the graft and wall of the blood vessel.

Accordingly, there is believed to be a need for an improved surgical stapler which may be inserted longitudinally within a blood vessel (e.g., a vein or artery), or some other body tube, which may be moved longitudinally therealong to a desired location relative to the blood vessel, which may be selectively articulated relative to the longitudinal axis of the blood vessel, and which may be thereafter operated so as to, first, drive the prongs of a U-shaped staple through an object and into the blood vessel wall, and to, secondly, bend or deform the inserted staple such that the staple cannot unintentionally separate from the blood vessel wall.

DISCLOSURE OF THE INVENTION

With parenthetical reference to the corresponding parts, portions or surfaces of the disclosed embodiment, for purposes of illustration, the present invention broadly provides an improved articulatable stapler (e.g., 20) having a distal end adapted to be inserted into the body of a patient, such as within a blood vessel. The improved stapler includes: an elongated catheter (e.g., 21) having a distal end (e.g., 22) dapated to be inserted within the body of the patient and having a proximal end (e.g., 23); the distal marginal end portion of the catheter having a plurality of segments (e.g., 25,26,28), each of the segments being mounted for movement (e.g., pivotally) relative to its immediate neighboring segment such that the distal end face of the catheter may be selectively articulated between a first position at which the longitudinal axis of the most-distal segment (e.g., 28) is substantially aligned with the longitudinal axis of the catheter main body portion (24) and a second position at which the longitudinal axis of the most-distal segment is arranged at a substantial angle (e.g., 90°) with respect to the catheter main body portion longitudinal axis; articulating means for selectively moving the segments relative to one another between the first and second positions; and stapling means mounted on the distal marginal end portion of the catheter and selectively operable to cause the sharpened prongs of a staple to penetrate an object and the blood vessel wall and further operable to bend or deform the so-inserted staple so as to prevent unintended separation thereof from the blood vessel wall.

Accordingly, the general object of this invention is to provide an improved surgical stapler.

Another object is to provide an improved surgical stapler which is adapted to be inserted longitudinally into a blood vessel, and used to staple an object (e.g., tissue, a graft, etc.) to the interior surface of the blood vessel wall.

Another object is to provide an improved surgical stapler having an articulatable distal end portion which may be moved from a longitudinally-aligned position to a transversely-aligned position.

Still another object is to provide an improved articulatable surgical stapler which may be inserted longitudinally within a patient's blood vessel, articulated to a transversely-aligned position, used to staple one object (e.g., tissue, graft, etc.) to the blood vessel wall, and to thereafter deform the inserted staple to prevent unintended separation from the blood vessel.

These and other objects and advantages will become apparent from the foregoing and ongoing written specification, the drawings, and the appended claims.

Brief Description of the Drawings

FIG. 1 is a fragmentary front elevation of the improved stapler, this view showing the catheter main body portion, and showing the three series-connected segments forming the articulatable distal marginal end portion of the catheter, this view also showing the distal marginal end portion as being in its longitudinally-oriented first position.

FIG. 2 is a fragmentary right side elevation of the improved stapler shown in FIG. 1.

FIG. 3 is a right side elevation, generally similar to FIG. 2, but showing the distal marginal end portion of the stapler as having been articulated to its traversely-oriented second position.

FIG. 4 is an enlarged front elevation of one of the intermediate segments shown in FIG. 1.

FIG. 5 is a right side elevation of the intermediate segment shown in FIG. 4.

FIG. 6 is an enlarged front elevation of the most-distal segment shown in FIG. 1.

FIG. 7 is a vertical sectional view thereof, taken generally on line 7—7 of FIG. 6, showing the most-distal segment in central longitudinal cross-section, this view also showing the anvil as being in its retracted position.

FIG. 8 is a view generally similar to FIG. 7, but showing the anvil as having been moved upwardly to its extended position relative to the most-distal segment, and engaging the cross-bar of a staple held in a ready position on the most-distal segment.

FIG. 9 is a fragmentary vertical sectional view of the most-distal segment, taken generally on line 9—9 of FIG. 8, showing the force members as being in their retracted positions.

FIG. 10 is a view generally similar to FIG. 9, but shows the force members as having been partially extended so as to engage the ends of the staple cross-bar.

FIG. 11 is a view generally similar to FIG. 10, but shows the force members as having been further extended to bend the marginal end portions of the staple about the anvil.

FIG. 12 is a view showing the improved stapler as having been inserted within a blood vessel, and as having been articulated to its second position and being used to staple a graft to the inside wall of a blood vessel.

MODE(S) OF CARRYING OUT THE INVENTION

At the outset, it should be clearly understood that like reference numerals are intended to identify the same structural elements, portions or surfaces consistently throughout the several drawings figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Referring now to the drawings, this invention broadly provides an improved articulatable intravascular stapler, of which the presently-preferred embodiment is generally indicated at 20. Stapler 20 is shown as being in the form of a vertically-elongated catheter 21 having an uppermost distal end 22 adapted to be inserted into, and moved generally longitudinally along, a blood vessel or other tubular passage of a patient (i.e., either human or animal) through a suitable incision (not shown). The catheter also has a proximal end 23 which is adapted to remain outside the patient's body.

More particularly, catheter 21 is shown as having a main body portion 24, and a plurality of series-connected segments, severally indicated at 25,26,28, operatively arranged between the main body portion and distal end 22. The main body and each segment is shown as having an axis of elongation. These several axes are severally indicated at y—y, and are individually further identified by the subscripts of the associated part. Thus, catheter main body 24 has a longitudinal axis $y_{24}$—$y_{24}$; next-higher segment 25 has a longitudinal axis $y_{25}$—$y_{25}$; next-higher segment 26 has a longitudinal axis $y_{26}$—$y_{26}$; and most distal segment 28 has a longitudinal axis $y_{28}$—$y_{28}$. The various adjacent segments are pivotally connected such that the longitudinal axis of the most-distal segment 28 may be selectively moved between a first position (i.e., as shown in FIGS. 1 and 2), at which axes $y_{24}$—$y_{24}$, $y_{25}$—$y_{25}$, $y_{26}$—$y_{26}$ and $y_{28}$—$y_{28}$ are substantially-aligned, and a second position (i.e., as shown in FIG. 3) of which most-distal segment axis $y_{28}$—$y_{28}$ is arranged at a substantial angle (e.g., 90°) with respect to catheter main body axis $y_{24}$—$y_{24}$. The improved stapler is further shown as including articulating means, generally indicated at 29, for selectively moving the most-distal segment 28 between its first and second positions, and stapling means, generally indicated at 30 mounted on the most-distal segment for holding a staple in a ready position (i.e., as shown in FIGS. 8–11) such that the legs thereof project beyond the distal end 22, and for selectively bending the staple so as to close the same.

As best shown in FIGS. 1 and 2, the catheter main body portion 24 is depicted as being a vertically-elongated cylindrical rod, which may be formed of a suitable plastic material so as to render it relatively flexible to movement in a transverse direction (i.e., as shown in FIG. 12). In other words, the catheter is formed of a suitable material, and has a sufficient length-to-diameter ratio as to allow it to bend or flex as it is slidably inserted, and moved longitudinally along, a blood vessel or other tube within the body. In FIGS. 1 and 2, the much-elongated shape of the catheter body portion is somewhat abbreviated by the broken lines, and does not appear in its full longitudinal extent. Nevertheless, an approximation of such elongation is shown in FIG. 12.

In any event, the catheter main body portion 24 is depicted as having an elliptical planar upper end face 31 inclined at an acute included angle of θ with respect to the horizontal, the circular horizontal proximal end face 23, and an outer cylindrical surface 32 extending therebetween. As best shown in FIGS. 1 and 2, an inclined notch extends into the catheter main body portion so as to communicate upper face 31 with outer surface 32. More particularly, this notch is defined by a pair of horizontally-spaced facing vertical side walls, with upwardly- and rightwardly-facing inclined surface 33 (FIG. 2) extending therebetween and communicating upper face 31 with outer surface 32. A horizontal hole 34 is provided through the upper marginal end portions of the catheter main body portion so as to intersect this notch. Hole 34 is adapted to receive a suitable pin (not shown) by which next-higher segment 25 may be pivotally mounted to lower body portion 24.

The lower body portion is provided with a plurality of longitudinally-extending internal passageways, each of which extends between upper end face 31 and proximal end face 23. More particularly, these passageways include a horizontally-elongated rectangular slot-like passageway 35, cylindrical passageways 36,38 and an additional cylindrical passageway 39 forward of slot 35. An additional horizontally-elongated slot 40 is arranged immediately behind slot 35 for a purpose hereinafter explained.

Intermediate segments 25 and 26 are structurally identical to one another. Hence, in the interest of brevity of description, only one of these segments will be explicitly described, it being understood that the other segment is identically configured. Therefore, referring to FIGS. 4 and 5 intermediate segment 25 is shown as being a vertically-elongated solid member provided with planar inclined elliptical upper and lower faces 41,42, respectively. In the preferred embodiment, each of surfaces 41,42 is inclined at an acute inclined angle θ with respect to the horizontal. In the preferred embodiment described herein, angle θ is approximately 15°. The outer peripheral edges of upper and lower end faces 41,42 are joined by an outwardly-facing cylindrical side surface 43. As with the catheter main body portion, segment 25 is provided with a notch joining upper surface 41 with cylindrical side wall 43. More particularly, this notch is shown as being bounded by horizontally-spaced facing left and right planar vertical surfaces 44,45 (FIG. 4), and by an upwardly- and rightwardly-facing inclined notch bottom surface 46 (FIG. 5) extending from upper face 41 to outer surface 43. In addition to this, the two marginal portions of the segment on either side of this slot are provided with aligned holes, pivotally indicated at 48, to accommodate a pin (not shown) by which segment 25 may be pivotally mounted to on next-higher segment 26.

As clearly shown in FIGS. 4 and 5, intermediate segment 25 is provided with a horizontally-elongated rectangular vertical through-slot 49 which is adapted to be vertically aligned with main body portion slot 35 when the catheter is in its first position shown in FIGS. 1 and 2. Segment 25 is also provided with three vertical through-holes 50,51,52, which are similarly aligned with catheter main body portion holes 36,38,39, respectively, when the catheter is in its first position. Another horizontally-elongated rectangular vertical through-slot 53 connects upper and lower faces 41,42, and is aligned with catheter lower body portion slot 40 when the catheter is in its first position. A horizontally-elongated eye 54 extends downwardly from the lower rear marginal end portion of lower face 42. This eye appears to be in the form of a horizontally-elongated tube having its left and right annular vertical end faces 55,56 adapted to be received between the facing walls of the slot of the catheter lower body portion. This eye is provided with a horizontal through-bore 58 which is adapted to be aligned with holes 48,48 on segment 25, and to accommodate passage of an intermediate portion of the pin (not shown) by which segment 25 may be mounted on lower body portion 24. Moreover, while slot 53 is shown as being of non-varying transverse cross-section along its vertical length, slot 49 is shown as having a somewhat trapezoidal shape or configuration when seen (FIG. 5) in a direction transverse to horizontal longitudinal axis $x_{25}$—$x_{25}$, for a purpose hereinafter explained. Segment holes 50,51,52, as well as segment slot 53, may be of substantially the same cross-sectional shape and configuration as lower body portion holes 36,38,39, and lower body slot 40, respectively.

Next-higher segment 26 is identical to segment 25, just described. Persons skilled in the art will readily appreciate that the eye of segment 26 is adapted to be received in the slot of next-lower segment 25, in the manner that the eye of segment 25 is received in the slot of the body lower portion 24.

Referring now to FIGS. 1, 2 and 6–11, the most-distal segment 28 is shown as having a circular horizontal upper end face or distal end 22, a lower inclined elliptical planar end face 59 also inclined at angle θ with respect to the horizontal, and an outwardly-facing cylindrical side wall surface 60 extending vertically therebetween. Upper segment 28 is shown as having a forward internal spherical socket 61 from which a vertical hole 62 depends to join lower face 59. When the catheter is in its first position, as shown in FIGS. 1 and 2, hole 62 is aligned with, but spaced from, hole 52 of next-lower segment 26. In this form, the articulating means is shown as being in the form of a stylet having an uppermost spherical ball 63 received within spherical recess 61, and as having a flexible stylet portion 64 passing through hole 62, holes 52 of intermediate segments 26 and 25, and hole 39 of catheter main body portion 24. Stylet 64 is shown in FIGS. 1 and 2 as terminating in a lowermost ring 65. Hence, by pulling stylet 64 downwardly with respect to lower body portion 24, the most-distal segment 28 and intermediate segment 26 will be caused to pivot about the axes of holes 34 from the first position shown in FIGS. 1 and 2 to the second position shown in FIG. 3. Conversely, if stylet 64 is moved upwardly relative to lower portion 24, the articulatable upper marginal end portion of the catheter will be moved from its second position back toward its first position.

The most-distal segment 28 is shown as having a pair of left and right vertical through-openings 66,68 which are adapted to be spaced from, but aligned with, holes 50,51, respectively, of next-lower segment 26. The upper marginal end portions of holes 66,68 are shown as being in-turned, as indicated at 69,70, respectively. As best shown in FIGS. 9–11, the invention is shown as further including force means in the form of two muchelongated stylets, severally indicated at 71,72, respectively. These stylets are threaded through lateral passages 36,38,50,51,50,51, and 66,68. Stylets 71,72 have lower marginal end portions 73,74, respectively, extending downwardly below the proximal end portion 23 of the catheter. Hence, by grasping these marginal end portions the stylet may be moved longitudinally within the several passageways provided through the catheter main body portion and the several segments, between a retracted position shown in FIG. 9 and an extended position shown in FIG. 11. When a staple 75 is held in a ready position of the most-distal segment, as shown in FIG. 9, the stylets may be selectively moved from their retracted position to first engage the distal marginal end portions 76,78 of the staple horizontal cross bar 79. As shown in FIG. 11, the four stylets may be still further extended so as to cause the upstanding prongs 80,81 of the staple to bend inwardly about the anvil, as described infra.

Referring now to FIGS. 7 and 8, the most distal segment 28 is shown as having a horizontally-elongated rectangular through-slot 82, also seen as having a somewhat trapezoidal cross-section when seen in transverse cross-section, which slot is adapted to communicate with slot 53 of next-lower segment 26. Rectangular passageways 35,49, 49,82 are adapted to communicate with one another, albeit through interruptions, when the articulatable end portion is in its first position or in its second position. These passageways provide a common passageway by which a staple may be inserted into the proximal end of the catheter, and moved therealong to the distal end thereof.

Still referring to FIGS. 7 and 8, the most-distal segment 28 is shown as having a horizontally-elongated rectangular passageway therethrough. This passageway includes a lower portion 83, the lower marginal end portion of which is adapted to communicate with slot 53 in next-lower segment 26, and as having an upwardly-and inwardly-inclined upper portion 84 continuing upwardly therefrom to join distal end face 22. An anvil, generally indicated at 85 has a lower end portion extending downwardly beyond proximal end 23, has intermediate portions pass through slots 40,53,53,83 and 84, and has an upper marginal end portion 86 adapted to be moved between a retracted position (FIG. 7) which the anvil distal marginal end portion is concealed within upper curve passageway 84, and an extended position (FIG. 8) at which the anvil distal marginal end portion is operatively arranged to engage the upper surface of the cross bar of a staple 75 in its ready position. Thus, when the anvil is in its extended position, staple 75 may not exit the uppermost passageway 82.

Therefore, in use, stylet 71 may be moved relative to the catheter lower body portion 24 to selectively cause the upper or distal marginal end portion of the catheter to move between its first position (FIGS. 1 and 2) at which the longitudinal axis of the catheter main body portion and the several segments thereof are substantially aligned, and a second position (FIG. 3) at which the longitudinal axis of the most-distal segment 28 is substantially transverse to the longitudinal axis of the lowermost main body portion 24. Thus, the distal end face may be selectively moved to an arc distance of about 90° as it moves between its first and second positions.

Referring now to FIG. 12, a blood vessel (not fully shown) of a patient may be exposed, and an incision made therein to allow insertion of the distal end portion of the improved catheter. Once so inserted, the improved catheter is moved generally longitudinally along the blood vessel until it reaches a desired position. The position of the catheter relative to the blood vessel may be determined by well-known fluoroscopic techniques. In any event, once in position, the articulating means may be manipulated to cause the distal marginal end portion of the catheter to move from its first position to its second position, as shown in FIG. 12. A staple may then be moved longitudinally along the communicating staple feed passages, 35,49,49,82, and may be held by means of a plunger 88, and may be held in a ready position between the upper face of plunger 88 and the facing surface of extended anvil 85. Thereafter, the catheter may be manipulated so as to move the distal end portion thereof in a generally radially direction to cause the extended prongs 80,81 of the staple to penetrate an object, such as unfurled tubular graft 89 and the wall 90 of blood vessel 91. Thereafter, and with the anvil still extended, the force stylets may be selectively extended along the communicating passageways of the various segments, to bend or otherwise deform the marginal end portions of the staple about the distal end of anvil 85. After this has been done, the force means and anvil may be retracted, and the articulating stylet may be selectively extended to return the distal marginal end portion of the catheter to its first position. Thereafter, the catheter may be withdrawn from the blood vessel, and the incision through which entrance thereof was made, suitably closed.

Therefore, the invention broadly provides an improved articulatable intravascular stapler (20) which broadly includes an elongated catheter (21) having a distal end (22) adapted to be inserted into, and moved along, a blood vessel (e.g. 91) of a patient, the catheter also having a proximal end (e.g. 23) adapted to remain outside the patient's body. The catheter has a main body portion (24) and has a plurality of series-connected segments (25,26,28) arranged between the main body portion and the distal end. Adjacent segments are pivotally connected such that the longitudinal axis ($y_{2-8} - y_{28}$), may be selectively moved between a first position substantially aligned with the longitudinal axis of the blood vessel and the longitudinal axis of the lower body portion, and a second position arranged at a substantial angle (e.g., 90°) with respect to these axes. The improved stapler further includes articulating means (64) for selectively moving the most distal segment (28) between its first and second positions, and stapling means (30) mounted on the most distal segment for holding a staple in a ready position such that the legs thereof will project beyond the distal end of the catheter and for selectively bending the staple to close the same.

In use, the improved stapler performs the improved method of stapling an object, such as other tissue, a graft, or the like, to the interior wall of a blood vessel, which method includes the steps of: making an incision (not shown) in the blood vessel; inserting the distal end of an elongated catheter into the blood vessel, moving the catheter generally longitudinally along the blood vessel until the distal end is in a desired position relative thereto; articulating the distal marginal end portion of the catheter so that the longitudinal axis of the most-distal portion of the catheter is arranged at a substantial angle, such as 90°, with respect to the longitudinal axis of the blood vessel; holding a staple on the catheter most-distal portion in a ready position at which the legs of the staple extend beyond the distal end of the catheter; moving the catheter to cause the legs of the staple to penetrate at least a portion of the object and the wall of the blood vessel; and bending the staple to prevent the staple from unintentionally separating from the object and the blood vessel. The improved method may further include the additional steps of: releasing such bent staple from the catheter; articulating the catheter to a position at which the longitudinal axis of the most-distal portion thereof is substantially aligned with the longitudinal axis of the blood vessel; withdrawing the catheter from the patient's body through the incision; and closing the incision.

MODIFICATIONS

The present inventions contemplates that many changes and modifications may be made. For example, which the preferred embodiment is shown as having a main body portion and three segments, a greater or lesser number of segments may be employed, depending upon the particular application. Thus, while each of these various elliptical end faces of the segments are shown as being inclined in an angle $\theta$ of about 15° with respect to the horizontal, persons skilled in this art will readily appreciate that this angle may be readily changed, as desired.

Similarly, the articulatable means is not limited to a stylet which slidingly penetrates the catheter main body and two intermediate segments and is anchored in the most-distal segment. Indeed, other forms of causing the various segments to articulate or bend relative to one another may be employed. Also, for conceptual purposes, the various segments of the improved catheter are shown as being pivotally connected to one another by means of a clevis-like connection. This is not invariable, and may be readily changed. For example, the various segments could be joined by means of a flexible web or "living hinge" therebetween.

The force means and the anvil may also be varied to suit the particular type of stapling mechanism employed. Thus, while the disclosed embodiment is presently-preferred, a person skilled in the art will readily appreciate that various other types of stapling mechanisms might alternatively be employed.

The shape and configuration of the improved catheter may, therefore, be changed or modified as desired. The improved stapler may be used to join one object to the inside wall of a blood vessel. Such object may be other tissue, a graft or some other object or element.

Therefore, while a preferred form of the improved stapler has been shown and described, and several modifications thereof discussed, a person skilled in this art will readily appreciate that various additional changes and modifications may be made without departing from the spirit of the invention, as defined and differentiated by the following claims.

I claim;

1. An articulatable intravascular stapler, comprising:
    an elongated catheter having a distal end adapted to be inserted into, and moved along, a blood vessel of a patient, said catheter also having a proximal end adapted to remain outside the patient's body;
    said catheter having a main body portion and having a plurality of series-connected segments arranged between said main body portion and said distal end, adjacent segments being pivotally connected such that the longitudinal axis of the most-distal segment may be moved between a first position substantially aligned with the longitudinal axis of said blood vessel and a second position arranged at an angle with respect to said blood vessel axis;
    articulating means for selectively moving said most-distal segment between said first and second positions; and
    stapling means mounted on said most-distal segment for holding a staple in a ready position such that the legs thereof project beyond said distal end and for selectively bending the staple to close the same.

2. An articulatable intravascular stapler as set forth in claim 1 wherein said distal end portion includes three of said segments.

3. An articulatable intravascular stapler as set forth in claim 1 wherein said articulating means includes a cable slidably mounted on said catheter, said cable having one end secured to said most-distal segment and having an opposite end extending outside the body and adapted to be manipulated to selectively move said most-distal segment between said first and second positions.

4. An articulatable intravascular stapler as set forth in claim 1 wherein said second portion is inclined at an angle of about 90° with respect to said blood vessel axis.

5. An articulatable intravascular stapler as set forth in claim 1 wherein said stapling means includes an anvil mounted on said most-distal segment for movement between an extended position, at which said anvil is adapted to engage the cross-bar of a staple in said ready position, and a retracted position at which said anvil will not engage said cross-bar.

6. An articulatable intravascular stapler as set forth in claim 5 and further comprising at least one force member mounted on said catheter for selective movement relative thereto, and operatively arranged to relatively bend a portion of a staple in said ready position about said anvil.

7. An articulatable intravascular stapler as set forth in claim 6 and further comprising two of said force members mounted on said catheter for selective movement relative thereto, and operative to bend different portions of a staple in said ready position about said anvil.

8. An articulatable intravascular stapler as set forth in claim 1 and further comprising guide means within said catheter and extending from the proximal marginal end portion to said distal end for guiding longitudinal movement of a staple along said catheter.

9. An articulatable intravascular stapler as set forth in claim 8 wherein said stapling means includes an anvil mounted on said most-distant segment for movement between an extended position, at which said anvil is adapted to engage the cross-bar of a staple in said guide means and in said ready position, and a retracted portion at which said anvil will not engage said cross-bar and will permit a staple in said guide means and in said ready position to exit said catheter by passing through said distal end.

10. An articulatable intravascular stapler as set forth in claim 8 and further comprising plunger means operatively arranged to move a staple along said guide means toward said ready portion.

11. The method of stapling an object to the interior wall of a blood vessel, comprising the steps of:
    making an incision in the blood vessel;
    inserting the distal end of an elongated catheter into said blood vessel;
    moving said catheter along said blood vessel until said distal end is in a desired position relative to said blood vessel;
    articulating the distal marginal end portion of said catheter so that the longitudinal axis of the most-distal portion of said catheter is arranged at a substantial angle with respect to the longitudinal axis of said blood vessel;

holding a staple on said catheter to a ready position at which the legs of said staple extend beyond said distal end;

moving said catheter to cause the legs of said staple to penetrate at least a portion of said object and the wall of said blood vessel; and bending said staple to prevent said staple from unintentionally separating from said object and blood vessel.

12. An articulatable intravascular stapler as set forth in claim 11 and further comprising the additional steps of:

releasing such bent staple from said catheter;

articulating said catheter to a position at which the longitudinal axis of said distal marginal end portion is substantially aligned with the longitudinal axis of said blood vessel;

withdrawing said catheter from the patient's body through said incision; and closing said incision.

* * * * *